(12) United States Patent
Hall et al.

(10) Patent No.: US 11,881,313 B2
(45) Date of Patent: Jan. 23, 2024

(54) CUSTOMIZED QUESTIONS FOR USER OF ANALYTICAL TOILET

(71) Applicant: Medic, Inc., Provo, UT (US)

(72) Inventors: David R. Hall, Provo, UT (US); K. Jeffrey Campbell, Spanish Fork, UT (US)

(73) Assignee: Hall Labs LLC, Provo, UT (US)

( * ) Notice: Subject to any disclaimer, the term of this patent is extended or adjusted under 35 U.S.C. 154(b) by 216 days.

(21) Appl. No.: 17/383,852

(22) Filed: Jul. 23, 2021

(65) Prior Publication Data

US 2022/0028559 A1 Jan. 27, 2022

Related U.S. Application Data

(60) Provisional application No. 63/055,595, filed on Jul. 23, 2020.

(51) Int. Cl.

| | |
|---|---|
| *G16H 50/30* | (2018.01) |
| *G16H 10/20* | (2018.01) |
| *G01N 33/483* | (2006.01) |
| *G16H 20/00* | (2018.01) |
| *E03D 5/014* | (2006.01) |
| *G16H 40/67* | (2018.01) |

(52) U.S. Cl.
CPC .............. *G16H 50/30* (2018.01); *E03D 5/014* (2013.01); *G01N 33/483* (2013.01); *G16H 10/20* (2018.01); *G16H 20/00* (2018.01); *G16H 40/67* (2018.01)

(58) Field of Classification Search
CPC ........ G16H 50/30; G16H 10/20; G16H 20/00; G16H 40/67; G16H 50/20; E03D 5/014; G01N 33/483; A61B 10/0038; A61B 10/007; Y02A 90/10
USPC ........................................................ 705/2–3
See application file for complete search history.

(56) References Cited

U.S. PATENT DOCUMENTS

2015/0000025 A1 * 1/2015 Clements ................ G06F 3/041
4/443
2019/0212322 A1 * 7/2019 Tsuruoka ............. A61B 5/6887

FOREIGN PATENT DOCUMENTS

WO WO-2019213424 A2 * 11/2019 ........... A47K 17/026

* cited by examiner

*Primary Examiner* — Joy Chng

(57) ABSTRACT

The present disclosure relates to methods for obtaining health and wellness information about individuals and systems for implementing the method. In one embodiment, a method for obtaining health and wellness information about an individual comprising providing an analytical toilet comprising a bowl adapted to receive excreta from the individual and a sensor for measuring at least one characteristic of the individual or the excreta; a controller receiving data from the sensor and using that data to determine what additional information is needed to evaluate that data; the controller sending a prompt to the individual to solicit the additional information from the individual; the processor receiving the information from the device; and processing the data from the sensor and from the device to determine the health and wellness information is disclosed.

20 Claims, 9 Drawing Sheets

“CUSTOMIZED QUESTIONS FOR USER OF ANALYTICAL TOILET”

CROSS-REFERENCE TO RELATED APPLICATIONS

This application claims the benefit under 35 U.S.C. 119(e) of U.S. Provisional Patent Application No. 63/055,595 titled "Customized Survey for User of Analytical Toilet" filed on 23 Jul. 2020, which disclosure is incorporated herein by reference in its entirety.

TECHNICAL FIELD

The present disclosure relates to analytical toilets. More particularly, it relates to analytical toilets equipped to provide health and wellness information to the user.

BACKGROUND

The ability to track an individual's health and wellness is currently limited due to the lack of available data related to personal health. Many diagnostic tools are based on examination and testing of excreta, but the high cost of frequent doctor's visits and/or scans make these options available only on a very limited and infrequent basis. Thus, they are not widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. At that point, preventative care may be eliminated as an option leaving only more intrusive and potentially less effective curative treatments. An ounce of prevention is worth a pound of cure.

Just a few examples of smart toilets and other bathroom devices can be seen in the following U.S. Patents and Published Applications: U.S. Pat. No. 9,867,513, entitled "Medical Toilet With User Authentication"; U.S. Pat. No. 10,123,784, entitled "In Situ Specimen Collection Receptacle In A Toilet And Being In Communication With A Spectral Analyzer"; U.S. Pat. No. 10,273,674, entitled "Toilet Bowl For Separating Fecal Matter And Urine For Collection And Analysis"; US 2016/0000378, entitled "Human Health Property Monitoring System"; US 2018/0020984, entitled "Method Of Monitoring Health While Using A Toilet"; US 2018/0055488, entitled "Toilet Volatile Organic Compound Analysis System For Urine"; US 2018/0078191, entitled "Medical Toilet For Collecting And Analyzing Multiple Metrics"; US 2018/0140284, entitled "Medical Toilet With User Customized Health Metric Validation System"; and US 2018/0165417, entitled "Bathroom Telemedicine Station." The disclosures of all these patents and applications are incorporated by reference in their entireties.

Data and subsequent analysis from a toilet can be used directly to assess a user's health and/or wellness. Other times, additional context (i.e., recent meals, exercise) may help in coming to a more accurate assessment of the user's health and/or wellness. Some of this context may come in the form of answers to questions or prompts posed to a user. For example, a user's heart rate may be elevated above normal for many reasons, including a health condition which may be of concern as well as having just participated in strenuous physical activity.

SUMMARY

In a first aspect, the disclosure provides a method for obtaining health and wellness information about an individual comprising providing an analytical toilet comprising a bowl adapted to receive excreta from the individual and a sensor for measuring at least one characteristic of the individual or the excreta; a controller receiving data from the sensor and using that data to determine what additional information is needed to evaluate that data; the controller sending a prompt to the individual to solicit the additional information from the individual; the processor receiving the information from the device; and processing the data from the sensor and from the device to determine the health and wellness information.

In a second aspect, the disclosure provides a system for obtaining health and wellness information about an individual comprising an analytical toilet comprising a bowl adapted to receive excreta from the individual and a sensor for measuring at least one characteristic of the individual or the excreta; a controller that receives data from the sensor and using the data to determine what additional information is needed to evaluate the data; a prompt to the individual to solicit the additional information; and the controller receives responses from the individual and uses the responses to further analyze the sensor data.

Further aspects and embodiments are provided in the foregoing drawings, detailed description, and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
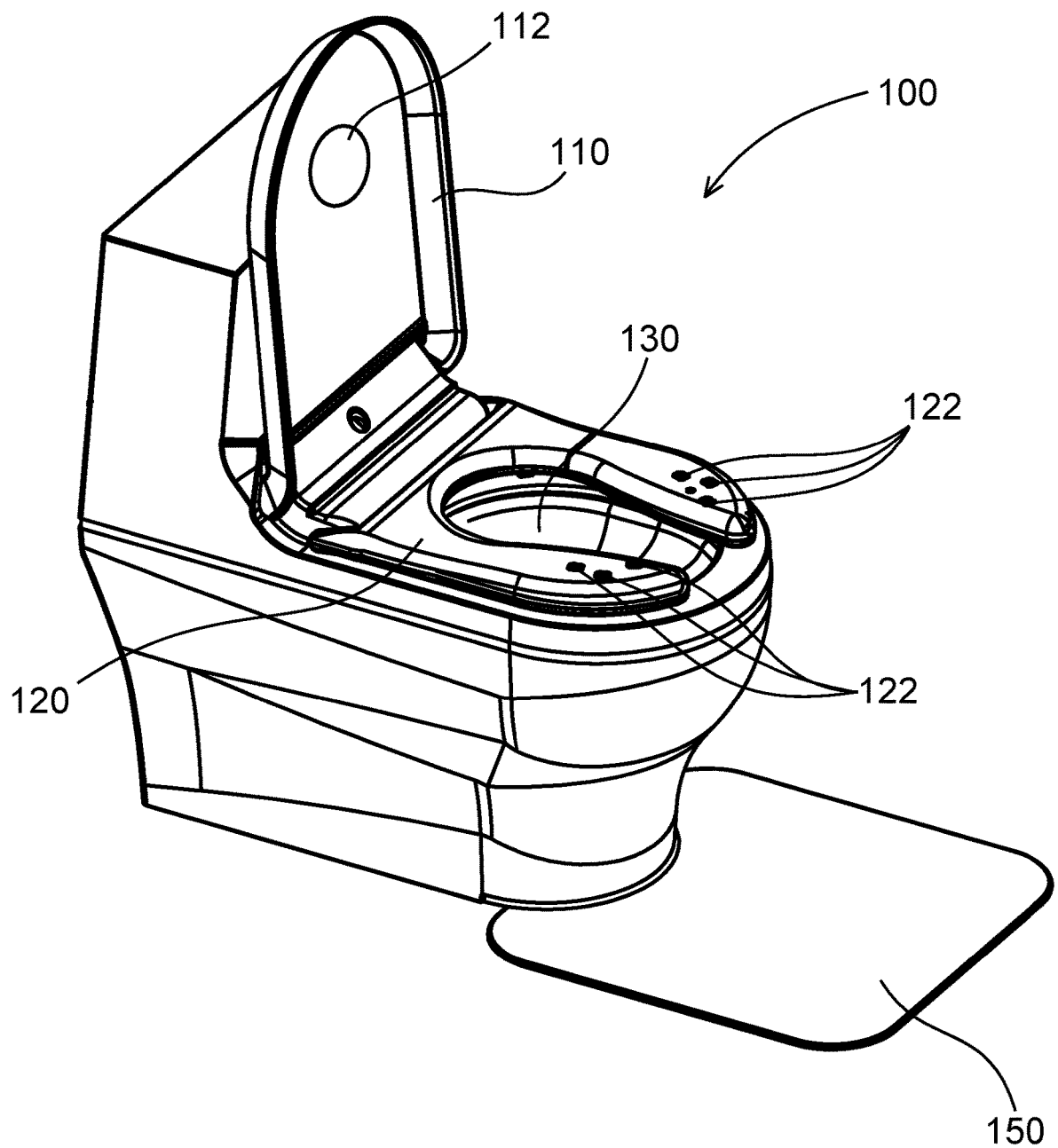
FIG. 1 is an isometric view of one embodiment of a toilet.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "toilet" is meant to refer to any device or system for receiving human excreta, including urinals.

As used herein, the term "bowl" refers to the portion of a toilet that is designed to receive excreta.

As used herein, the term "base" or "frame" refers to the portion of the toilet below and around the bowl supporting it.

As used herein, the term "user" refers to any individual who interacts with the toilet and deposits excreta therein.

As used herein, the term "excreta" refers to any substance released from the body of a user including urine, feces, menstrual discharge, saliva, expectorate, and anything contained or excreted therewith.

As used herein, the term "excretion profile" is meant to refer collectively to the rate of excretion at any moment in time of an excretion event and the total volume or mass of excreta as a function of time during an excretion event. The terms "defecation profile" and "urination profile" refer more specifically to the separate measurement of excreta from the anus and urethra, respectively.

As used herein, the term "sensor" is meant to refer to any device for detecting and/or measuring a property of a person or of a substance regardless of how that property is detected or measured, including the absence of a target molecule or characteristic. Sensors may use a variety of technologies including, but not limited to, MOS (metal oxide semiconductor), CMOS (complementary metal oxide semiconductor), CCD (charge-coupled device), FET (field-effect transistors), nano-FET, MOSFET (metal oxide semiconductor field-effect transistors), spectrometers, volume measurement devices, weight sensors, temperature gauges, moisture gauge, chromatographs, mass spectrometers, IR (infrared) detector, near IR detector, visible light detectors, and electrodes, microphones, load cells, pressure gauges, PPG (photoplethysmogram), thermometers (including IR and thermocouples), rheometers, durometers, pH detectors, scent detectors gas, and analyzers.

As used herein, the term "imaging sensor" is meant to refer to any device for detecting and/or measuring a property of a person or of a substance that relies on electromagnetic radiation of any wavelength (e.g., visible light, infrared light, x-ray) or sound waves (e.g., ultrasound) to view the surface or interior of a user or substance. The term "imaging sensor" does not require that an image or picture is created or stored even if the sensor is capable of creating an image.

As used herein, the term "data connection" and similar terms are meant to refer to any wired or wireless means of transmitting analog or digital data and a data connection may refer to a connection within a toilet system or with devices outside the toilet.

As used herein, the terms "biomarker" and "biological marker" are meant to refer to a measurable indicator of some biological state or condition, such as a normal biological processes, pathogenic processes, or pharmacologic responses to a therapeutic intervention. Some biomarkers are related to individual states or conditions. Other biomarkers are related to groups or classifications or states or conditions. For example, a biomarker may be symptomatic of a single disease or of a group of similar diseases that create the same biomarker.

As used herein, the term "analyte" is meant to refer to a substance whose chemical constituents are being identified and measured.

As used herein, a "fluidic circuit" is meant to refer to the purposeful control of the flow of a fluid. Often, this is accomplished through physical structures that direct the fluid flow. Sometimes, a fluidic circuit does not include moving parts.

As used herein, the term "manifold" is intended to have a relatively broad meaning, referring to a device with multiple conduits and valves to controllably distribute fluids, namely water, liquid sample and air.

As used herein, the term "test chamber" is meant to refer broadly to any space adapted to receive a sample for testing, receive any other substances used in a test, and apparatus for conducting a test, including any flow channel for a fluid being tested or used for testing.

As used herein, a "fluidic chip" is meant to refer to a physical device that houses a fluidic circuit. Often, a fluidic chip facilitates the fluid connection of the fluidic circuit to a body of fluid.

As used herein, the term "microfluidics" is meant to refer to the manipulation of fluids that are contained to small scale, typically sub-millimeter channels. The prefix "micro" used with this term and others in describing this invention is not intended to set a maximum or a minimum size for the channels or volumes.

As used herein, the prefix "nano" is meant to refer to something in size such that units are often converted to the nano-scale for ease before a value is provided. For example, the dimensions of a molecule may be given in nanometers rather than in meters.

As used herein, "FET" is meant to refer to a field effect transistor, which is a device which uses an electric field to control the current flowing through a device. FETs are also known by the name "unipolar transistor".

As used herein, "biomarker" and "biological marker" are meant to refer to a measurable indicator of some biological state or condition, such as a normal biological processes, pathogenic processes, or pharmacologic responses to a therapeutic intervention. Some biomarkers are related to individual states or conditions. Other biomarkers are related to groups or classifications or states or conditions. For example, a biomarker may be symptomatic of a single disease or of a group of similar diseases that create the same biomarker.

As used herein, "bind" and similar variants are meant to refer to the property of facilitating molecular interaction with a molecule, such as interaction with a molecular biomarker.

As used herein, "functionalize" and similar variants are meant to refer to a device, especially a nanometer scale device, the surface of which being configured to interact with a specific analyte, such as a specific biomarker.

As used herein, "genomic derived signal" is meant to refer to a molecule generated by the genome of a cell, bacteria, virus, or other nucleic acid carrier, such as DNA, RNA, microRNA, cell-free (circulating) nucleic acids or those of various immunologically related cells.

As used herein, an analyte that "interacts" with a sensor is meant to refer to several ways a component (e.g., receptor) of a sensor can detect the analyte. "Interacting" may include reversible binding of an analyte to a component in a sensor. This may also be referred to as labile binding where the analyte is weakly bound to a component in the sensor and can be removed by a removal treatment such as a flushing or cleaning process. "Interacting" may include irreversible binding of an analyte to a component in a sensor where the binding is a one-time event and the component of the sensor or the entire sensor must be replaced after each use. "Interacting" may include a non-binding event wherein the analyte is in the vicinity of the component of the sensor such that the magnetic, optical or electrical properties of the component are perturbed by the presence of an analyte. For example, this may be caused by negative or positive charges located on the surface of the analyte.

As used herein, "tremor", "body tremor", and similar variants are meant to refer to involuntary motion, particularly those related to repeated muscle contraction and relaxation leading to shaking movements in one or more parts of the body. This shaking may be considered rhythmic or cyclical because of the fairly consistent and repetitive motion of the tremor.

As used herein, "physiologic tremor" and its derivatives are meant to refer to a fine tremor resulting from normal body function such as heartbeat, maintaining a posture, and movement. Occurrence of these is normal and generally not cause for seeking additional health or wellness care.

As used herein, "exacerbated physiologic tremor", "noticeable physiologic tremor", and their variants are meant to refer to a physiologic tremor which has become more pronounced than normal and is generally an indication of factors which may warrant health or wellness consideration or care, such as extreme fatigue, stress, intense emotion, low blood sugar (hypoglycemia), an overactive thyroid, medications such as corticosteroids, amphetamines or beta-agonists, heavy metal toxicity, stimulants such as caffeine, fever, and alcohol withdrawal.

As used herein, "symptomatic tremor", "abnormal tremor", "atypical tremor", and their variants are meant to refer to exacerbated physiologic tremors. They also include tremors whose existence is symptomatic, suggestive of, or correlates with an abnormal or atypical health or wellness condition, which condition may warrant additional care or consideration. It includes tremors that correlate with abnormal conditions and circumstances such as multiple sclerosis, stroke, traumatic brain injury, neurodegenerative diseases that affect parts of the brain (such as Parkinson's disease), use of certain medicines (including particular asthma medication, amphetamines, caffeine, corticosteroids, and some drugs used for psychiatric and neurological disorders), alcohol abuse or withdrawal, mercury poisoning, an overactive thyroid, liver or kidney failure, and anxiety or panic.

In general, "weight" refers to the force excreted by a physical object or organism, especially a person or animal, under the influence of a gravitational field. As used herein, "weight" is sometimes used to represent the more general term "force", which represents the mass of the physical object or organism multiplied by the acceleration of that mass. On the surface of Earth, gravity applies a relatively constant acceleration to mass thereon, thus creating the force of weight people are generally familiar with. When measured, the weight or force itself is generally not directly measured, but reaction forces acting in opposition to the weight or force are being measured.

The force exerted by a tremor is created by motion of one part of a person's body relative to another part of the body. While gravity does not control amount of force, it may influence the final measurement of the force. Thus, the force exerted by a tremor may be measured in a gravity environment different from that of a person on the surface of the earth so long as the effects of environment's gravity are accounted for by the system. This includes environments termed "weightless" wherein the person or environment is in a state of falling relative to large gravity objects in the vicinity (such as being in a diving aircraft or in orbit around a planet), resulting in the sensation of being free of gravity. As such, the force being measured to detect a tremor from a person is more dependent on the person's movements than from the gravitational pull of Earth; this force may manifest as a temporary change to measured weight. Thus accelerometers, while not the simplest way to measure the weight of a person at rest on Earth, are an acceptable form of weight sensor to detect the cyclical loading and unloading of forces associated with tremors. In short, this disclosure is not meant to limit the invention to applications at rest on the surface of a planet or other environment with similar gravity.

As used herein, "foot support" and similar terms are meant to refer to a structure designed to receive force from a person's foot, feet, and/or lower leg(s). This includes a structure that limits a single degree of freedom, such as one that rests on a floor and feet are placed thereon, as well as a structure meant to limit multiple degrees of freedom, such as a foot, ankle, or lower leg restraint.

As used herein, "symptom" is meant to refer broadly to any physiological characteristic of a patient. The characteristic may be indicative of an injury, illness, or disease (e.g., presence of an infection, high or low body temperature, involuntary muscle tremors, high or low analyte levels) but is not limited to those. The characteristic may also be indicative of the user or non-use of a treatment including, but not limited to, medication, physical therapy, or exercise. Such characteristic may include analytes in the patient's system indicative of the user or non-use of medication. Symptom also includes side-effects of a medicament or other treatment.

Exemplary Embodiments

The present disclosure relates to a system for assessing a user's health and wellness by taking sensor data when they use a toilet, using the data to decide on additional information or context for the data which the user can provide to improve the assessment, and prompting the user for the additional information.

The present disclosure relates to smart toilets with analytical tools (may also be referred to as an "analytical toilet"

or a "health and wellness toilet") which detect, analyze, and/or track the trends of analytes, such as biomarkers, of a user who deposits excreta into the toilet. More specifically, the toilet receives excreta from a user, processes the excreta in preparation for analysis, and brings a sample of excreta (including processed excreta) into a testing area for detection by nanometer scale circuitry component, BioFET, optical detector, or other similar testing components. The circuitry component has been functionalized to interact with a specific analyte, such as a biomarker, on a molecular or atomic level. The circuitry component provides a data signal depending on whether the specific analyte is present in the excreta sample in contact with it. After the toilet has finished with the excreta, the toilet purges the excreta from the toilet in preparation for receiving a new excreta sample.

One benefit of the present disclosure is that data can be given additional context by a user (or someone familiar with the user) to provide a more accurate assessment of a user's health and wellness. For example, analysis of data from the system may identify an anomaly that corelates with two or more of medical conditions, physical activities, and environmental factors. The user may be prompted for additional information to find out which, if any, of those correlated things are relevant to why the anomaly was detected.

As a more specific example, the general population has an approximate range for a resting heart rate. If the sensors detect that a user has a significantly higher heart rate while using the system, the system may ask the user questions to determine if the heart rate is higher because of a long-term medical condition, because of recent physical activity, or because of a short-term medical condition. If the user regularly uses the system, the system may track the readings over the multiple uses to establish a baseline heartrate, and other characteristics, for the user. The system may then focus more on detecting deviations from the user's baseline rather than a population baseline. A similar scenario could be followed with nearly any property of the user detected by the system.

There are many different properties of a user that can be detected and/or measured and even more ways to detect those properties. Essentially, any characteristic of a person that can be qualitatively or quantitatively defined is a property that may be detected and measured by the system. Any device which helps qualitatively or quantitatively determine a property could serve as part of the system to sense the property and report it to the system.

The following US Patent and PROVISIONAL Patent Applications discuss various implementations of sensors which may be able to detect and or measure properties of a user in various embodiments of toilets: U.S. patent application Ser. No. 16/818,900 titled "Toilet with Vascular Health Reporting" filed 13 Mar. 2020; Provisional Application No. 62/979,803 titled "Analytical Toilet for Assessing Analytes in Excreta" filed 21 Feb. 2020; Provisional Application No. 62/993,648 titled "Analytical Toilet for Detecting Viruses in Feces" filed 23 Mar. 2020; and Provisional Application No. 63/002,200 titled "Analytical Toilet for Detecting Viruses in Urine" filed 30 Mar. 2020. Each of these applications are incorporated into the specification herein by reference in their entirety.

In a preferred embodiment, a user is presented with a questionnaire (similar to those commonly used by health care providers) about current and past medical conditions, medications (changes and compliance), patterns of physical activity, dietary content (e.g., natural and artificial sweeteners, salt, fat, fruits and vegetables), calorie consumption, hydration, alcohol or drug use, vitamin or supplement usage, and any other information useful for analyzing user health and wellness. In a more preferred embodiment, the user is periodically asked to update or amend their responses to the initial questionnaire with more current information. In various exemplary embodiments, the response to this questionnaire is used as a starting point for analysis of user health and wellness by the system in attempting to measure user characteristics and identify potential issues based on sensor measurements.

In a preferred embodiment, the system will regularly query or receive information from other devices that obtain relevant information about the user. These devices may include smart scales, smart watches, smart phones (e.g., health and fitness apps), home pulse and blood pressure monitors, etc. The information may include health and wellness information, such as pulse, and location information (e.g., user at a gym). In a preferred embodiment, the system also obtains relevant information from healthcare providers via secure channels with permission of the user and provider.

The sensors may interact directly with the user or their excreta. The sensors may also interact with a sample of excreta that has been isolated and treated with one or more of dilutants, reactants, dyes or other fluids prior to interacting with a sensor. The sensors may include measuring pulse, blood pressure, blood oxygenation, electrocardiography, body temperature, body weight, excreta content, excreta weight, excreta volume, excreta temperature, excreta density, excreta flow rate, and other health and wellness indicators. The sensors may include one or more of imaging cameras, spectrometers, volume measurement devices, weight sensors, temperature gauges, chromatographs, and gas analyzers.

In some preferred embodiments, data from a detected property is sent from a sensor to a controller which compares the data to a database of potential health and wellness conditions and uses the results of the comparison to create a list of health and wellness conditions that correlate with the data. This list may also be based on a combination of data from multiple sensors. Additionally, the list may be based on general population data and/or on historic user data, including trends, averages, and baselines. Let it be noted that there are many ways to create a list of correlating conditions. One way is to include every condition on the list and use the data to remove conditions from the list. An alternative method would work in the opposite direction where no conditions are on the list and the data is used to add items to the list. Additional methods may start with some items already on the list, others not on the list, and the data is used to toggle a condition between the on-list and off-list status. As time passes some combination of these methods may be used to add or remove conditions from a user's list. Additionally, the list may be stored for future use, such as being the initial list each time that user uses the system.

There are many ways to view the on-list/off-list status of a condition, including viewing a condition as completely on the list, completely off the list, or on some sort of on-list/off-list spectrum based on a statistical probability the user has the condition or based on the strength of the correlation between the likelihood a person has the condition and the user's data. Any of these approaches may be used. For simplicity's sake, the disclosure may focus on one method, such as removing items from the list, but this is not meant to limit the invention to that method of list creation or refinement.

Once compiled, the list of correlating conditions may be used to create a second list of other information which could help refine or improve the accuracy of the list of correlating conditions and improve the assessment of the user's health and wellness. A combination of detected conditions may be indicative of another condition that may or may not be directly testable (e.g., high sodium levels may indicate a risk of heart disease). The list of other information may be used to create prompts for the user to provide additional information to the system. The system can use any additional information provided by the user to adjust its assessment of the user's health and wellness (e.g., recent exercise to explain elevated pulse).

There are many ways to prompt the user. Essentially, a prompt is any stimulus to the user indicating the system would like additional information from the user. This could be as simple as a predetermined sign to perform an action—such as a vibration, blinking light, or sound—which the user can sense. The request can also include more complex requests, including that the user have additional analysis performed and/or input the results to the system. The request may come in the form of questions to assess the user's physical activity or user recognizable symptoms which may correlate with conditions on the correlated condition list. The prompt may come from any source the system is in communication with, including something integrated into a toilet, a device adjacent to the toilet, a user mobile device or app thereon, email, text or similar phone message, a phone call, a system report, or a second person who carries out the request on behalf of the system. The prompt may include a wide variety of requests, including a request that the user redo an action so a sensor may gather a fresh set of data or a request that the user answer questions on a survey. The format could involve one or more of a user's senses, including sight, touch, and sound.

In one preferred embodiment, the prompt is a simple, predetermined signal with an established meaning the user is expected to know. For example, the prompt may be a light on the toilet which turns on and/or off to convey the prompt. Alternatively, a needle on a dial changes where it is pointing to. More alternatively, a similar effect could be achieved with a speaker generating a noise or a vibrator or other source of haptic feedback with a predetermined interpretation. Any of these could be integrated into the toilet, a nearby device, or a mobile device.

In another preferred embodiment, the prompt uses a screen near the toilet to convey a message to the user. More preferably, the screen is part of a mobile device. Alternatively, the message is printed out, such as on a paper. In another alternative embodiment, the message comes from a speaker and is heard audibly. Alternatively, the message is conveyed through touch, such as may be accomplished through a device which generates brail touch text.

In one preferred embodiment, the prompt includes one or more questions selected for their likelihood of getting the desired additional information from the user. Alternatively, the prompt includes instructions for the user to follow and thereby provide the additional information.

In one preferred embodiment, the prompt for additional information is a result of both a standard information request (i.e., one always asked of the user) and a non-standard information request that is modified based on the sensor data (i.e., one that changes based on the assessment of the sensor data). For example, a standard information request may ask the user to input their user identification information. A small set of examples of non-standard requests includes: (a) asking if someone is diabetic and/or has taken their insulin based on a urine glucose measurement out of the normal range, (b) a question assessing recent (e.g., within 2-hours) physical activity because the person's heartrate, temperature, or skin moisture is higher than the normal range, (c) questions assessing a person's stress level because their blood pressure is high, (d) asking about hydration level or salt intake because sodium in their blood is high, (e) asking if the person is experiencing cold or flu symptoms because of pathogenetic markers found in their excreta, (f) asking if or when someone last took a medicament based on metabolites found in their excreta, (g) asking if they recently ate poppy seeds because of increased opioid markers in their excreta, and (h) asking if they feel faint because their blood pressure is low.

In an alternative embodiment, the user does not directly receive the prompt, but the prompt is given to another person and the person conveys the information request to the user.

There are many ways to receive additional information from the user. Essentially, any sensor which can communicate data to the system can be used to input data into the system. The user may actively engage with a sensor, someone may engage with a sensor on the user's behalf, or an alert may notify the user that a sensor has been engaged. The sensor may be any of the sensors integrated with the toilet, a nearby device, a mobile device, or an app.

A variety of input methods may be used to respond to prompts from the system. Common input methods include use of a touch screen, buttons, dials, microphones, image sensors, vibration sensors, and any of the previously referenced sensors which detect or measure a property of the user. To provide the information, user may respond to one or more questions or follow instructions to do something. Alternatively, the user may choose not to provide the information as prompted by the system.

Additionally, there are many ways to get additional context and information from a user (or from someone familiar with the user), such as prompting the user for input and/or allowing the user to give input. Prompts can come in many forms, including audio requests, visual requests, tactile requests, and any other way that communicates to the user that additional information is being requested. Some common ways of providing a request to a user include digital displays, analog displays, print outs, knobs, dials, buttons, switches, haptic feedback, vocalized questions; any of which may also be set up to double for user input. Input from users can also be provided in many ways, including a graphical user interface (GUI), vocal response, tactile input (e.g., pushing buttons, turning switches or dials), and visual input (e.g. provided to an image sensor).

In one preferred embodiment, the user receives prompts from a mobile device, such as a phone or tablet. More preferably, the mobile device has an app through which the system prompts the user for information. Still more preferably, the app includes the option for the user to input information into the app in response to the prompt. Alternatively, the system may make use of other cell phone features to prompt for and receive information from the user. This could come in the form of phone calls (including automated calls), text messages, or multimedia messages. Additionally, system integration with a user's mobile device opens up other user/system interactions that can further be used.

Once excreta has been deposited in the toilet, there are many ways it could be processed in preparation for testing and disposal. Some pretreatments include a filter, a centrifuge, dilution, or pH normalization. In one preferred embodiment, a portion of feces is separated from urine, mixed with water and/or a reagent, and presented to the component of a sensor for analysis. Following analysis, the sample is removed from the sensor, and the sensor is cleaned and/or sterilized in preparation for a new sample being presented to the component of the sensor.

There are many ways to incorporate the sensor into the toilet, the selection of which will depend on various factors, including ease of manufacture and maintenance, target market, physical constraints, frequency of use compared to other desired functions of the toilet, and cost. In one preferred embodiment, the sensor is built into a fluidic circuit. More preferably, the fluidic circuit is on a fluidic card. Still more preferably, the fluidic circuit on the fluidic card is a microfluidic circuit on a micro fluidic card. Preferably, the fluidic card is inserted into a slot or receptacle of the toilet which connects the fluid circuit on the card to the toilet's fluidic delivery system, enabling the card to receive the sample derived from the excreta. Alternatively, the sensor is part of a larger device that may be attached to the toilet, such as a device that processes and/or analyzes excreta. Alternatively, the sensor is built into the toilet rather than being on a card. Alternatively, the sensor is external to the remainder of the toilet and is connected to receive and/or return fluid from the toilet, such as may be accomplished by connecting the sensor to part of the toilet with tubes or pipes.

In a preferred embodiment, the sensor is functionalized to interact with a biomarker and produce a signal based on the presence and/or concentration of the biomarker. Often, this means the sensor is configured to respond to an individual molecule or even a specific molecular element or portion of a biomarker. Biomarkers that work well with this kind of sensor include immunological genomic derived signals, DNA genomic derived signals, RNA genomic derived signals, microRNA genomic derived signals, other genomic derived signals, proteins, carbohydrates, lipids, metabolites, and ionic concentrations. In some preferred embodiments, the component of the sensor amplifies the concentration of the targeted analyte. In other preferred embodiments, the component dilutes the concentration of the targeted analyte. In some preferred embodiments, the concentration is neither amplified nor diluted. Use of one category of tests to detect a particular analyte does not preclude use of another test category to detect or measure the same analyte.

It can be useful to group biomarkers. There are a variety of relevant groupings. For example, some groupings worth being considered are as follows: ionic or electrochemical, immunological, chromogenic, labeling or biotinylation, fluorescent binding, staining reactions, and transfection or genotypic. Regarding these groupings, the following list is not exhaustive but instead are select examples:

Ionic and electrochemical:
- The pH level can be useful as abnormal values are indicative of medical issues. It can be used to normalize urine concentration.
- Amperometry may be measured via ion selective membranes. Specific biomarkers to look for include calcium, sodium, and potassium.
- Detection of alpha-methylacyl-CoA racemase is helpful in the detection of prostate cancer.

Immunological:
- Finding Interleukin-8 level helps with the detection of protein overabundance, which can indicate infection.
- Detection of Albumin in urine is indicative of kidney disease.
- Detection of creatinine, a protein metabolite, is indicative of whether the liver is functioning properly. It can be used to calibrate other test results, e.g., albumin.
- Thrombin is indicative of blood clotting in the kidneys.
- Prostate cancer can be detected by testing for a prostate specific antigen.
- Detecting HIV p24 antigen helps in the detection of HIV disease.
- Neutrophil gelatinase-associated lipocalin (NGAL), a marker for renal disease, helps track disease progression and effectiveness of treatment.
- With a color reagent, the resulting colorimetric data can be indicative of a variety of conditions.
- Biliruben is indicative of gall stones, infection, and/or liver malfunction.
- Urobilinogen is indicative of liver diseases.
- Nitrites are indicative of a urinary tract infection (UTI).
- Ketones are useful in monitoring metabolism.

Chromogenic:
- *E. coli* detection helps determine if there's a bacterial infection.
- Thrombin detection is helpful as its presence in urine may indicate existence of a blood clot.

Labeling, biotinylation:
- Glucose detection and levels are helpful in understanding a variety of conditions and states.
- Detection of C-polysaccharide can be useful in determining pneumonia, respiratory infections, treatment effectiveness.

Fluorescent binding:
- Cancer can be detected using a general tool for fluorescein functionalized binding agents.
- Albumin (as noted above).
- Urinary metabolites are indicative of a variety of states and conditions.
- Coronavirus (severe acute respiratory syndrome (SARS), middle eastern respiratory syndrome (MERS), coronavirus disease 2029 (Covid-19)) cDNA fragments can be detected through DNA binding.
- TNF-alpha detection is indicative of autoimmune disorders.

Staining reactions:
- Urine cytology can be helpful. It is achieved through a variety of methods, including automated microscopy or AI driven cytology.

Transfection, genotypic:
- DNA from tumors, gene targeting, and RNA expression can be determined through various assays.

There are many variations on sensors that detect biomarker molecules or atoms that may be used in a health and wellness analytical toilet described herein.

Figure 2:
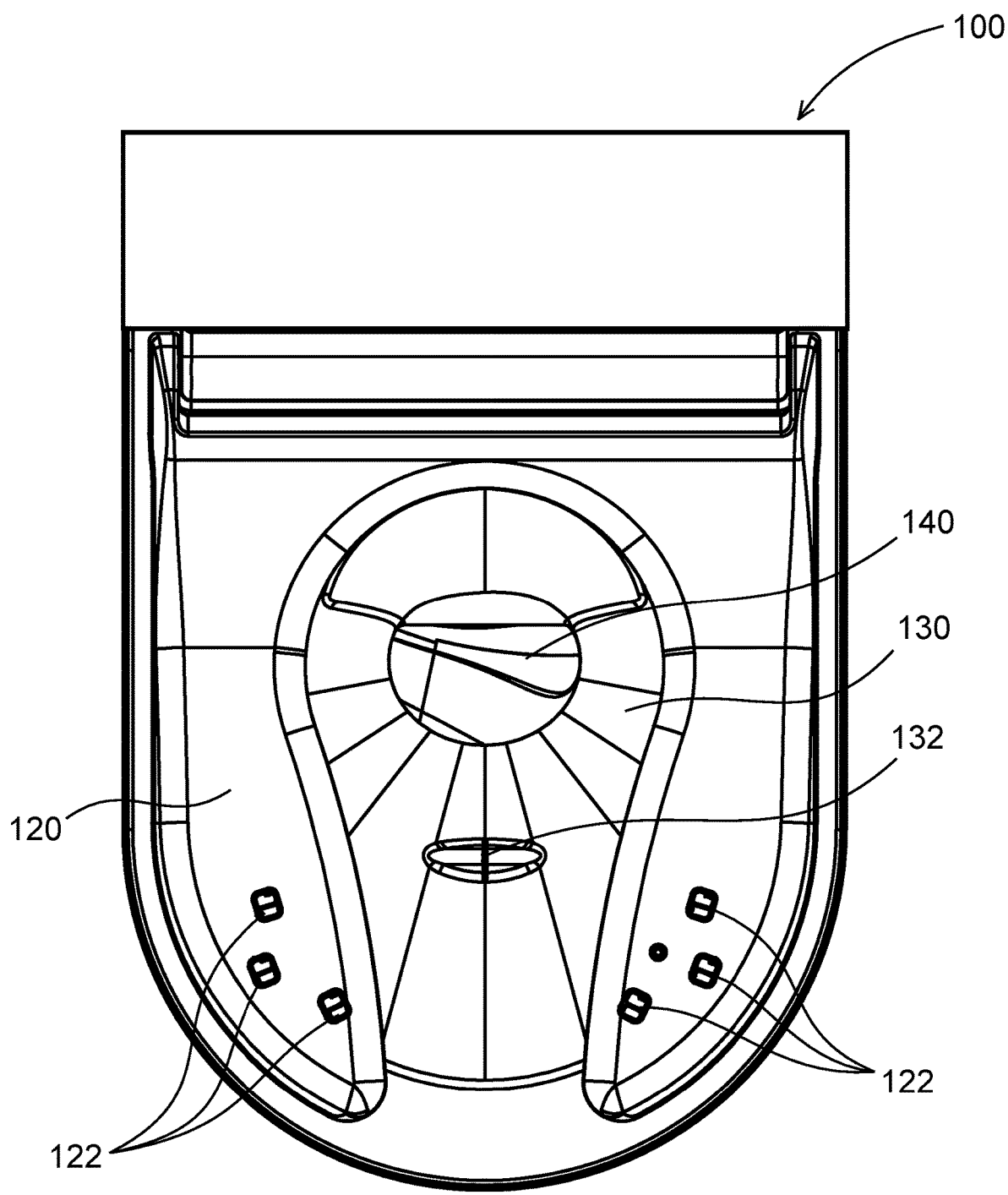
FIG. 2 is a top view of the toilet of FIG. 1.
Figure 3:
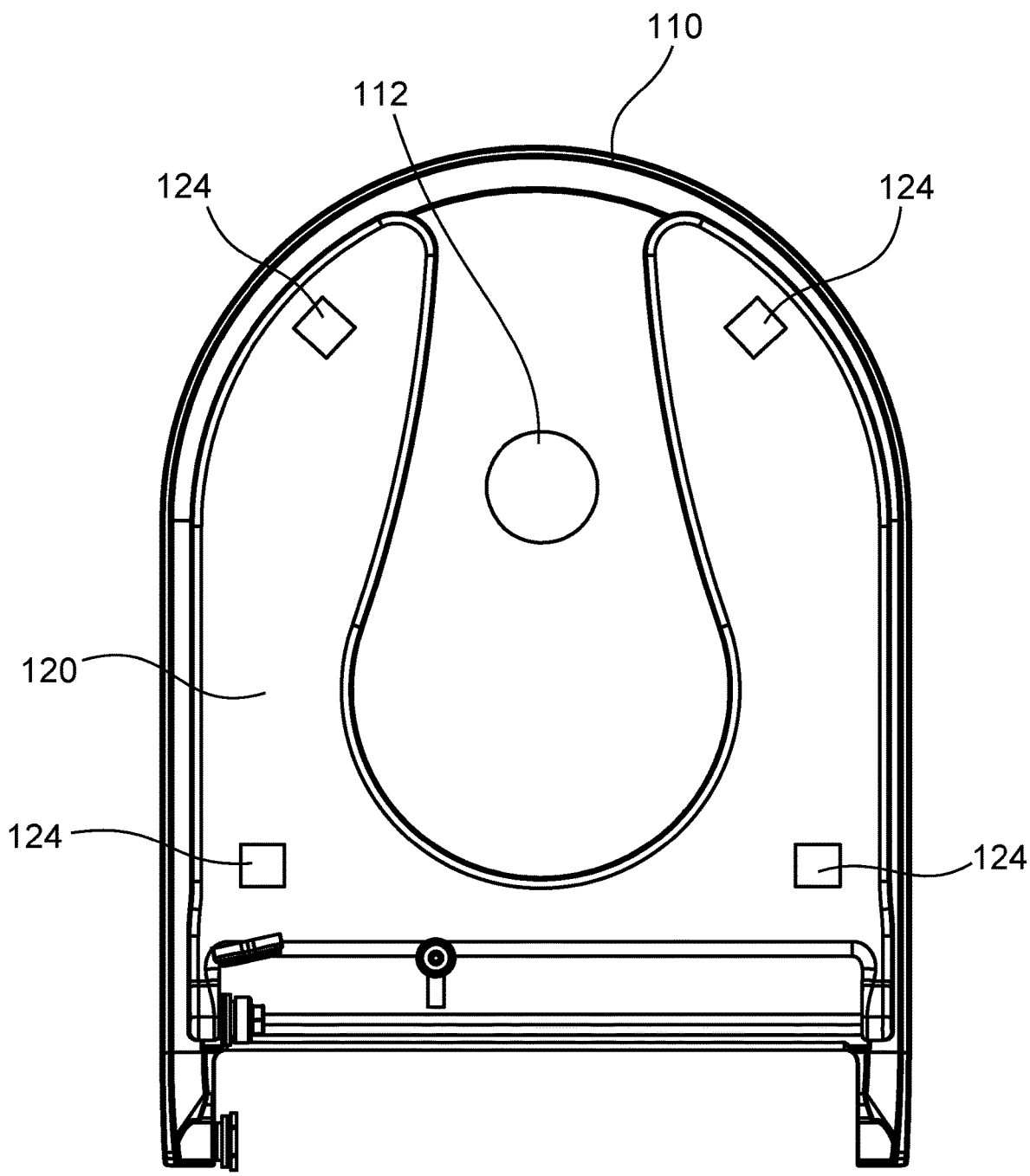
FIG. 3 is a view of the bottom of the seat and lid of the toilet of FIG. 1.
Figure 4:
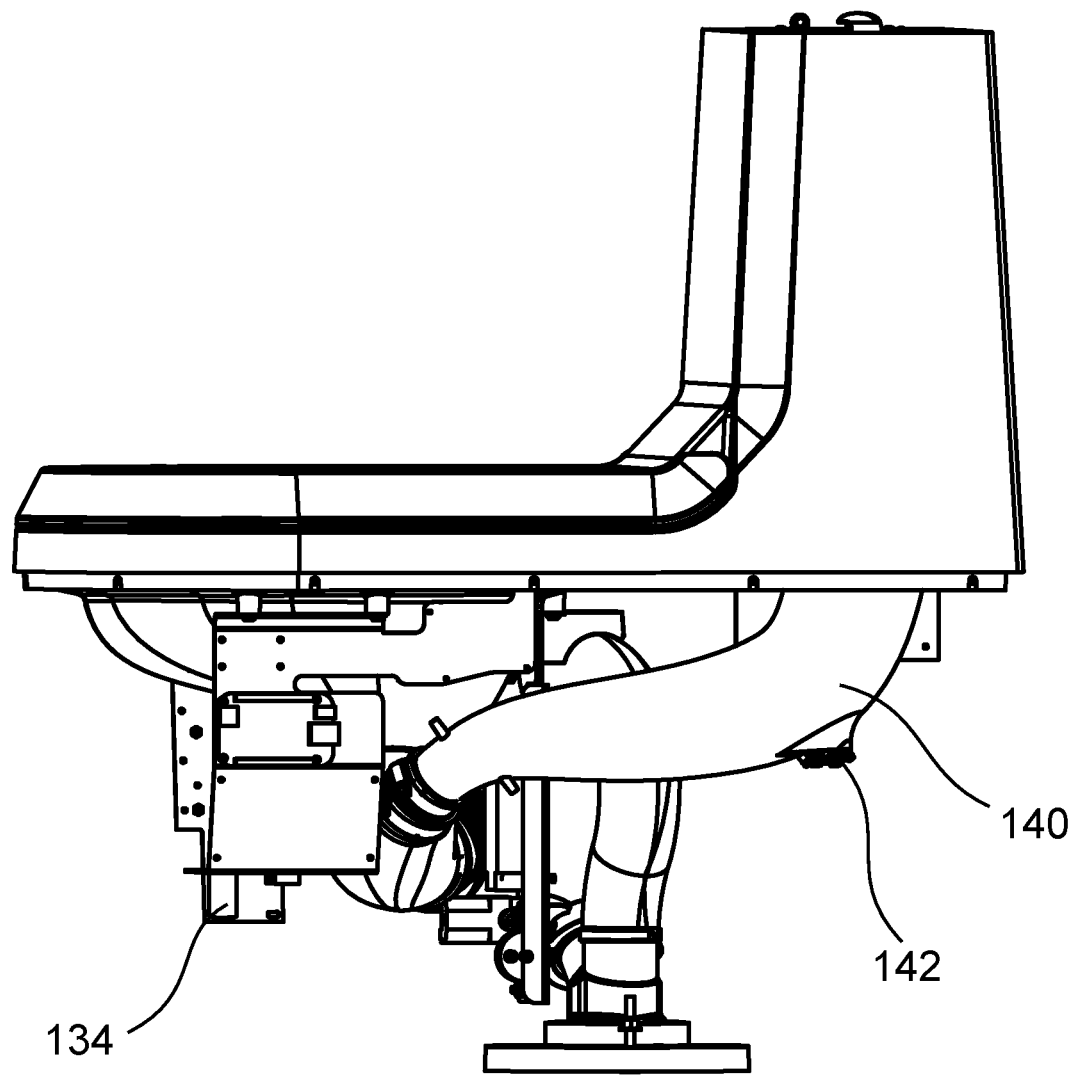
FIG. 4 is a view from the side of the toilet of FIG. 1 with the cover removed.

Now referring to FIGS. 1-4, one preferred embodiment of the toilet used in the system is shown. FIG. 1 shows an isometric view of toilet 100 with lid 110 open, showing seat 120 with multiple PPG sensors 122, bowl 130, and foot scale 150. Foot scale 150 may have a variety of sensors, such as sensors to determine a user's weight, image sensors, and electrical contacts. FIG. 2 shows a top view of toilet 100 with lid 110 open, showing seat 120 with multiple PPG sensors 122, bowl 130, and urine volume measure tube 140. Bowl 130 includes urine slit 132, which captures urine for readings by spectrometer 134. FIG. 3 is a detail view of the underside of seat 120 with lid 110 behind seat 120. On the underside of seat 120 are weight sensors 124. Shown on lid 110 is stethoscope 112, which includes a microphone for recording audio sounds from a user's trunk portion of the body. FIG. 4 is a detail view showing some of the internal components of toilet 100, including urine volume measure tube 140, urine tube volume sensor 142, and spectrometer 134. The toilet may also have other sensors to detect properties of a user or a user's excreta. The toilet may also have a way of sampling and testing the wastewater in the bottom of the bowl before and/or after it has interacted with excreta.

In one preferred embodiment, a user walks onto scale 150, and sits down on seat 120, leaving their feet on scale 150. While the user is using the toilet, PPG sensors 122 monitor the user's upper legs, weight sensors 124 monitor the portion of the user's weight on seat 120 (including minor, apparent fluctuations that are a result of a user's cardiovascular activity), weight sensors 154 monitor the portion of the user's weight on foot scale 150, and bioimpedance sensors 152 determine the user's bioimpedance.

Figure 5:
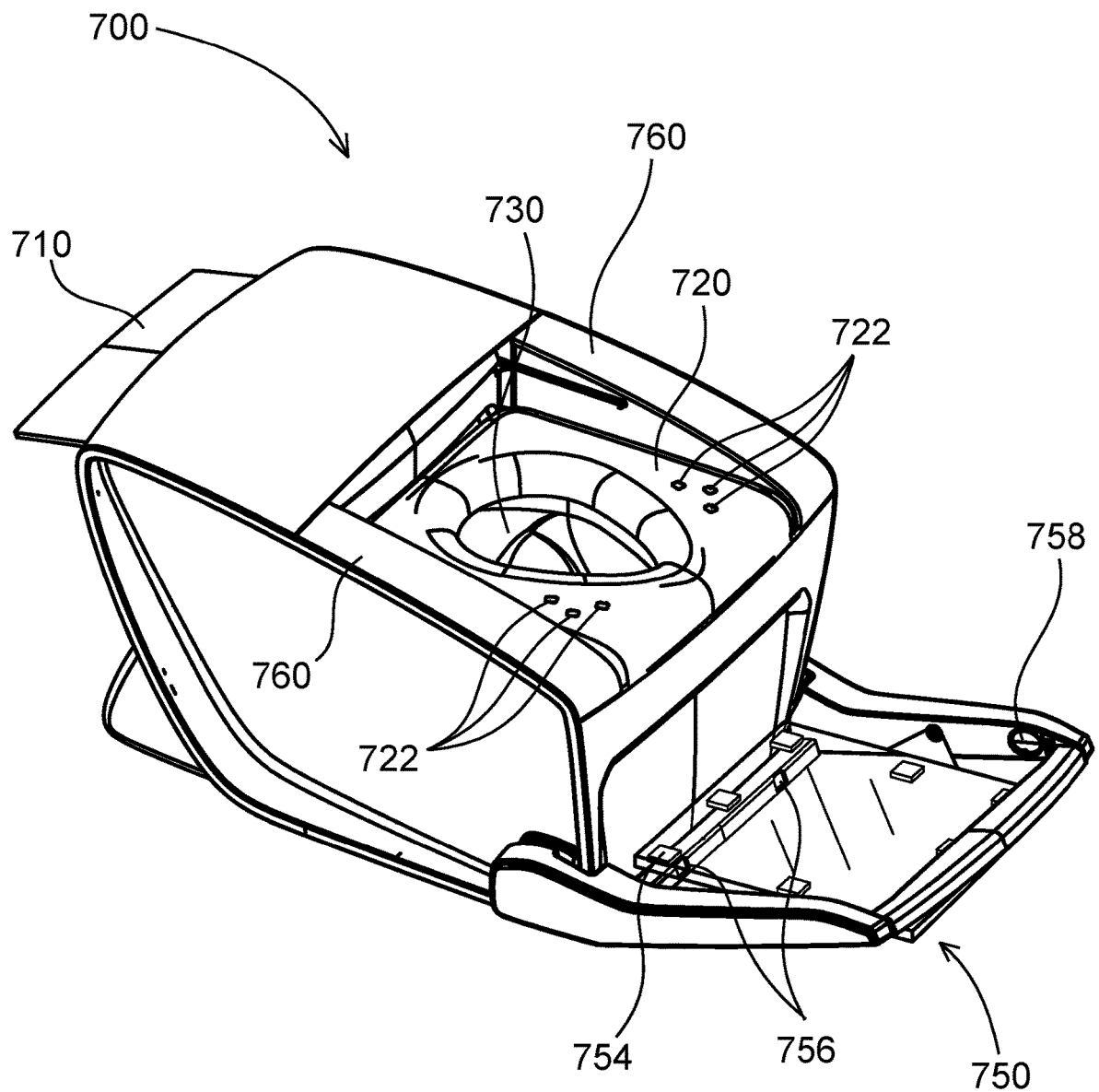
FIG. 5 is an isometric view of a second embodiment of a toilet.
Figure 6:
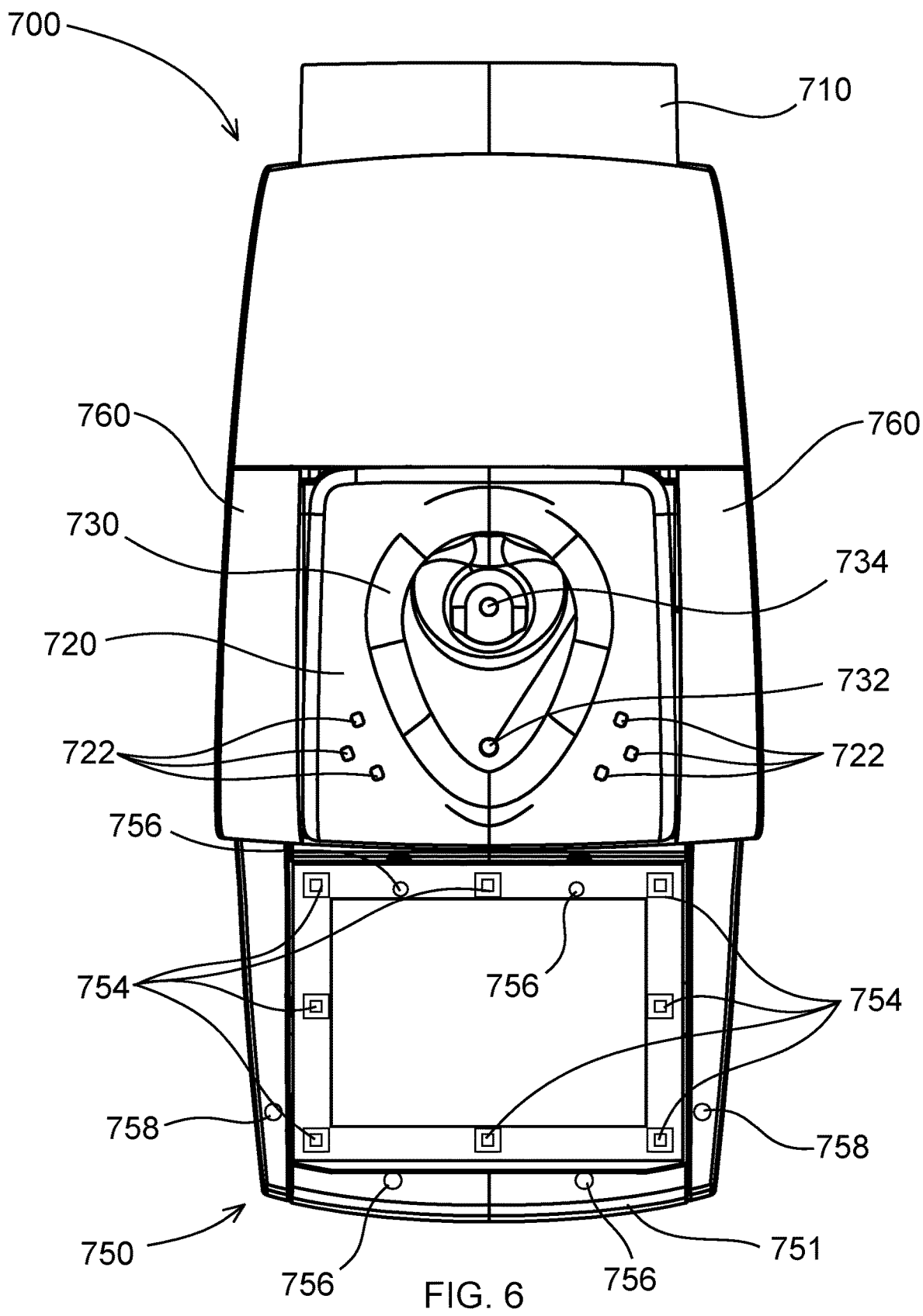
FIG. 6 is a top view of the toilet of FIG. 7.
Figure 7:
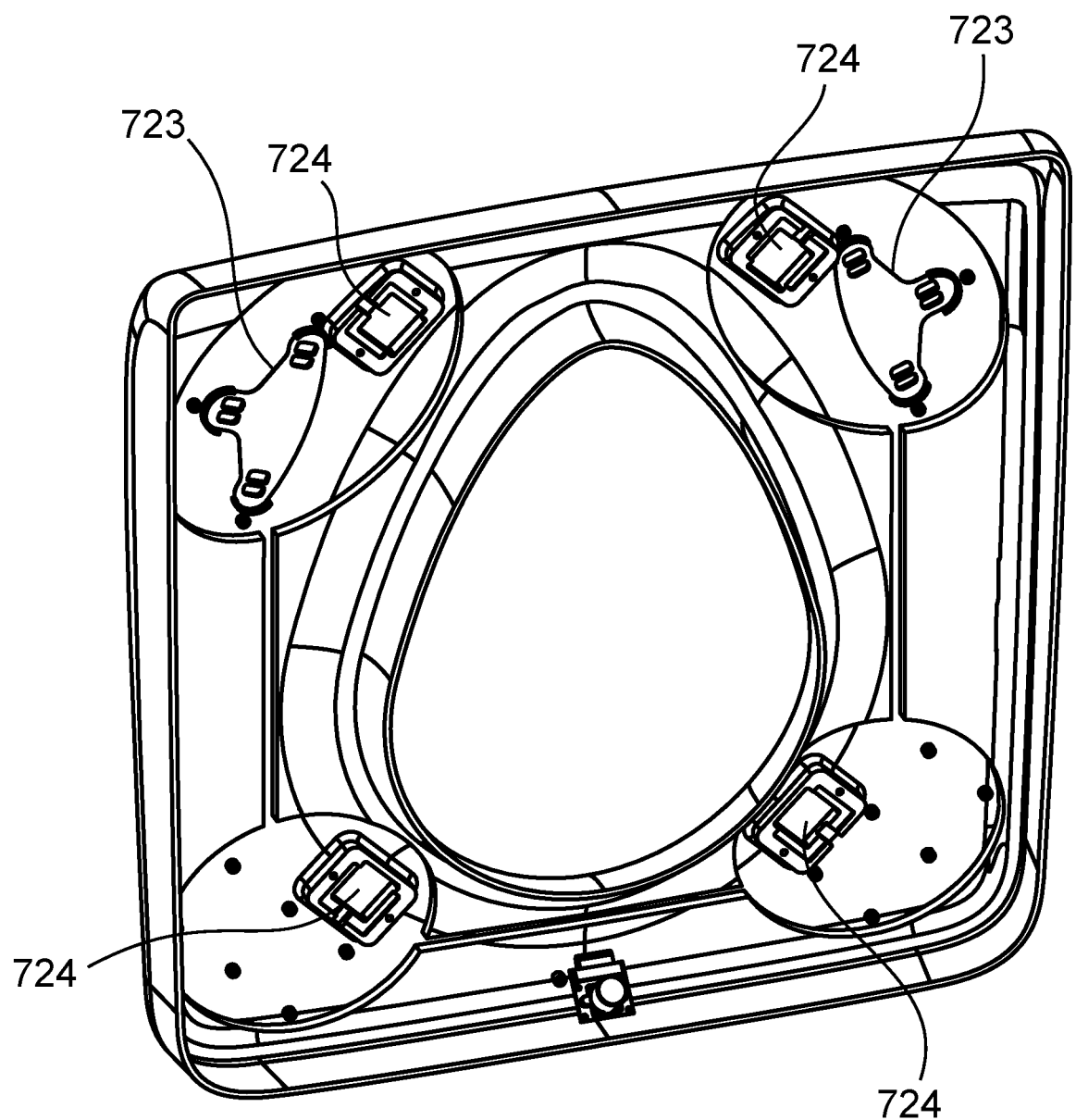
FIG. 7 is a view of the bottom of the seat of the toilet of FIG. 7.
Figure 8:
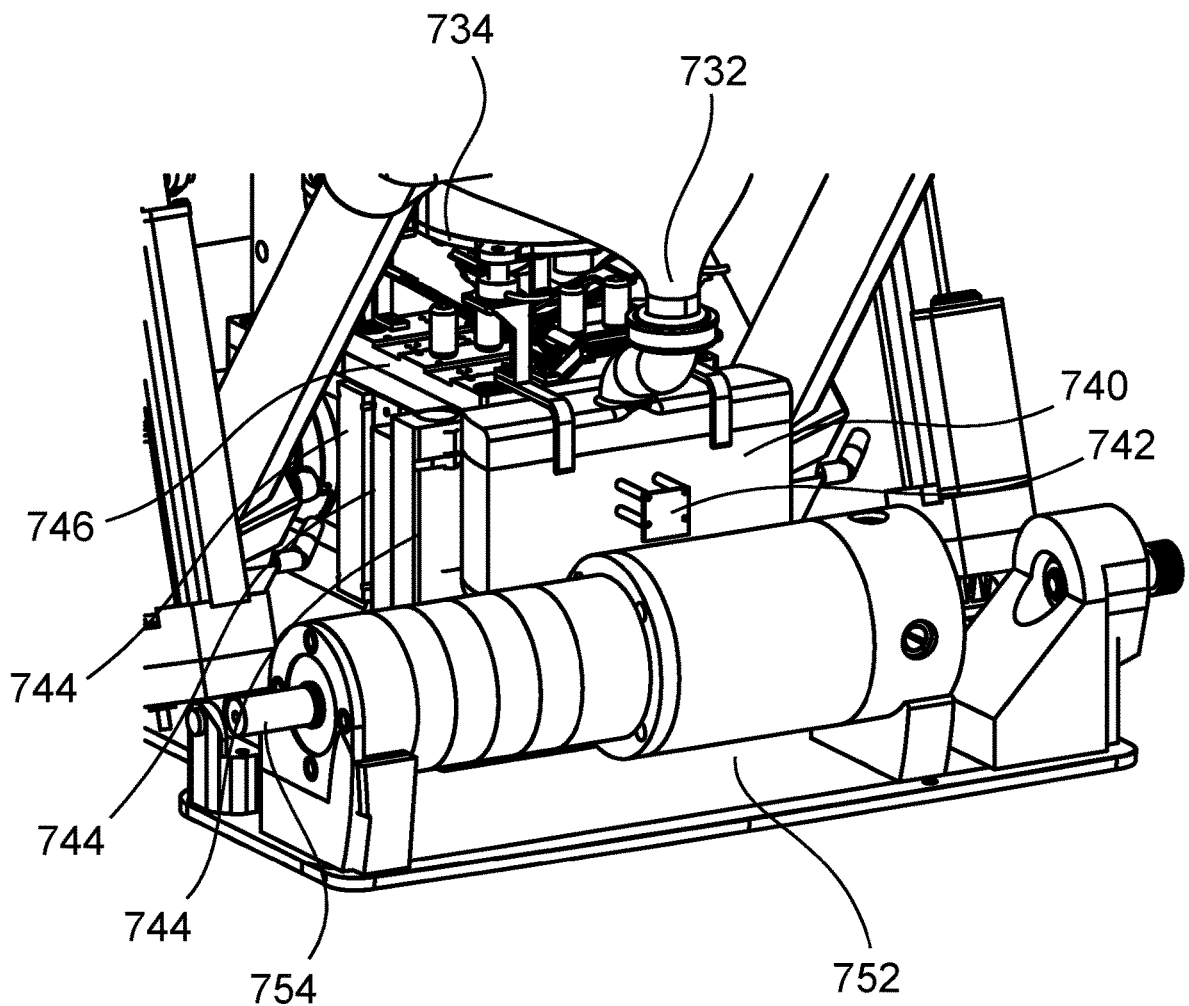
FIG. 8 is a partial view of the toilet of FIG. 7 with the cover removed.

FIGS. 5-8 show another embodiment of the toilet. FIG. 5 shows an isometric view of toilet 700 with lid 710 open, showing seat 720 with multiple PPG sensors 722, bowl 730, foot platform 750, and handles 760. FIG. 6 shows a top view of toilet 700 with lid 710 open, showing seat 720 with multiple PPG sensors 722, bowl 730, foot platform 750, and handles 760. Bowl 730 includes urine receptacle 732 and fecal depository 734. In one preferred embodiment, handles 760 are in a recessed position and can be raised up relative to the toilet. FIG. 7 is a detail view of the underside of seat 720 showing weight sensors 724. FIG. 8 is a detail view showing some of the internal components of toilet 700, including urine receptacle 732, fecal depository 734, urine volume measure chamber 740, urine spectrometer 742, science centers 744, fluid chip receptacle 746, foot platform motor and sensor 752, foot platform motor shaft 753. Foot platform 750 includes frame 751, a glass plate resting on multiple weight sensors 754, foot image sensors 756, and foot IR sensors 758. In one preferred embodiment, science centers 744 and fluid chip receptacle 746 are used in conjunction with excreta analysis, including urine samples and emulsified or otherwise processed excreta.

In one preferred embodiment, a user walks onto platform 750, sits down on seat 720, and platform 750 raises up so the user's feet easily stay on the glass plate. While the user is using the toilet, PPG sensors monitor the user's upper legs, weight sensors 724 monitor the portion of the user's weight on seat 720 (including minor, apparent fluctuations that are a result of a user's cardiovascular activity), weight sensors 754 monitor the portion of the user's on foot platform 750, and sensors 754 and 758 monitor the user's feet and lower legs. In one preferred embodiment, sensors 754 and 758 are able to detect properties of the foot, including foot size and shape, coloring, and subdermal vascular properties. These images can undergo image recognition analysis, the results of which can be compared to preexisting data on the same to generate a report on a user's health. Preferably, the report includes information relative to a user's vascular health. Preferably, the comparison is performed by a neural net which has been trained to recognize commonalities to and differences from preexisting images. When the preexisting images are coupled with known health states and/or conditions of the person from whom the images came, the neural net can suggest correlations between the user's images and health states and/or conditions (including neutral or positive ones). Additionally, when the neural net has examined previous data from the same user, the neural net can compare the user's prior state to his or her current state to report on the relative change. Therefore, it may be useful for user data to be averaged, have the mean taken, used in creating trend data, or otherwise be used in creating a baseline against which to compare new user data as it is generated.

Figure 9:
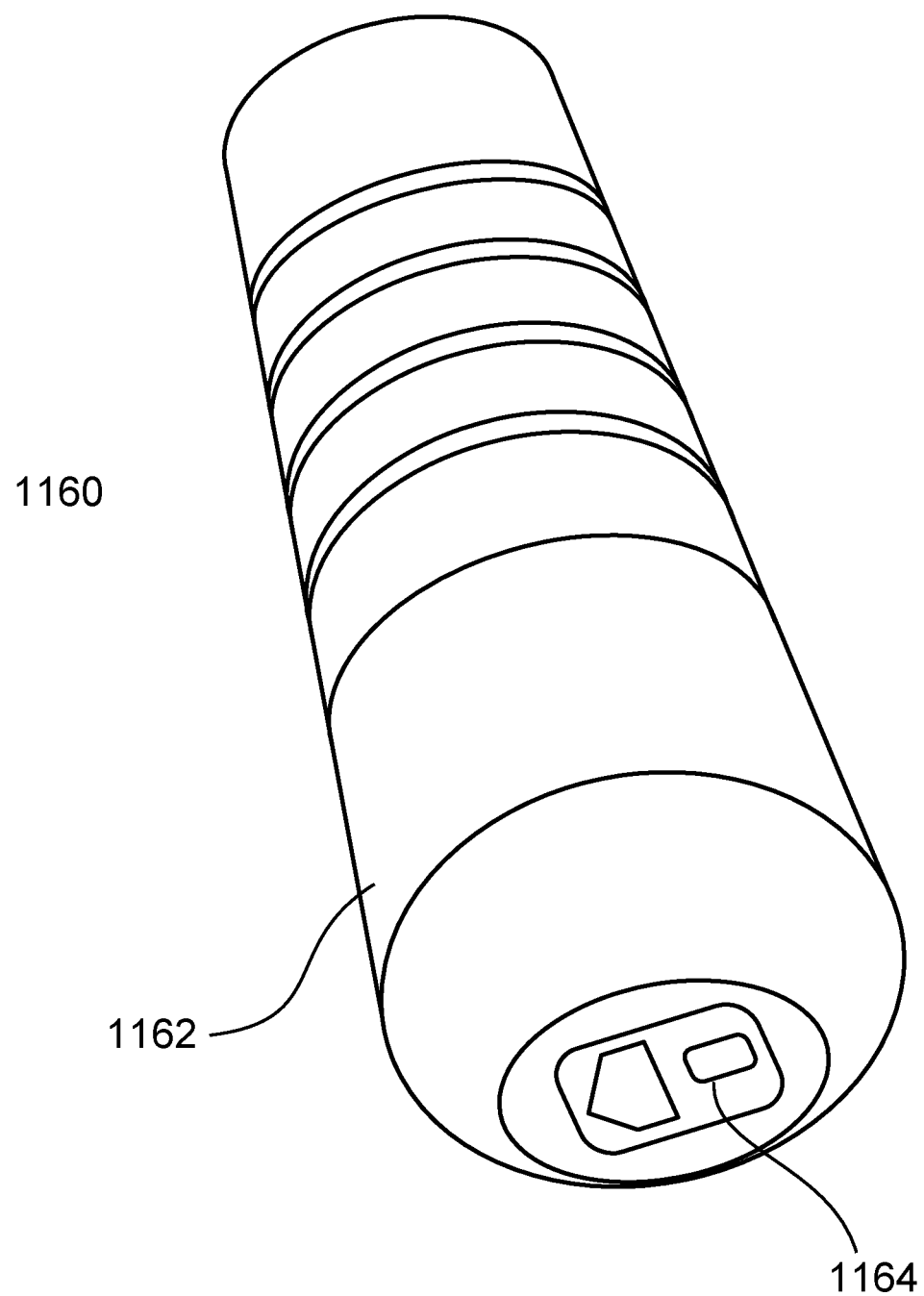
FIG. 9 is a detail view of one embodiment of a handle.

FIG. 9 shows an embodiment of a handle that could accompany a toilet. Handle 1160 includes electrical lead 1162 and PPG sensor 1164. Electrical lead 1162 could be a lead for a bioimpedance sensor and/or an ECG sensor. In one preferred embodiment, a handle would be connected to a cord (with wiring) that connects to the toilet. Alternatively, a handle could be wireless and in digital communication with a controller that is also in digital communication with other of the toilet sensors. And another preferred embodiment a handle would be mounted to a structure adjacent to the toilet bowl. In either embodiment a second handle they also do used. A second handle may originate from the same connection point to the toilet or a location symmetrically opposite or mirrored from the first handle.

One exemplary class of sensors are biosensor field-effect transistors (BioFETs). BioFETs are based on metal-oxide-semiconductor field effect transistors (MOSFETs) that are gated by changes in the surface potential induced by the binding of biomolecules. Complimentary metal-oxide-semiconductor field effect transistors (CMOSFETs) may also be used. BioFETs comprise a field effect transistor and a biological recognition element or receptor.

BioFET-based sensors for a health and wellness analytical toilet may comprise one or more nanowires or functionalized nanowires to bind with a biomarker, one or more nanocrystals or functionalized nanocrystals, one or more sheets of graphene or functionalized graphene or a combination thereof. These materials are placed in a manner in the FET to bridge the source and drain electrodes. The BioFET may comprise a semiconductor with a functionalized gate. Other sensors include colorimetric based assays, paper-based analytical devices, a luminescent markers or labels, and a fluorescent or otherwise optically stimulated marker or label.

In some embodiments, nanowires for use in BioFETs may include conducting polymers such as polythiophene, polyaniline, polycarbazole, poly(3,4-ethylenedioxythiophene), polypyrrole, polyphenol or combinations thereof. Nanowires may comprise metals such as germanium, silver, gold, platinum, nickel palladium or combinations thereof. Nanowires may comprise two or more metals in a core-shell like arrangement. The metallic nanowires may comprise a thin oxide surface layer for covalent attachment of biomarker receptors. Nanowires may include inorganic oxide materials such as indium oxide ($In_2O_3$), indium tin oxide (ITO), zinc oxide (ZnO), tin oxide (SnO), titania ($TiO_2$) or silica ($SiO_2$). In an exemplary embodiment, the nanowire comprises a non-functionalized or functionalized single walled carbon nanotube (SWCNT) or a non-functionalized or functionalized multi-walled carbon nanotube (MWCNT) or a combination thereof. In a more exemplary embodiment, the nanowire comprises silicon (Si). The Si nanowire may comprise p-type or n-type Si. The Si nanowires may have a diameter of about 2 nm or larger. In other embodiments, the Si nanowires may have a diameter of about 2-100 nm. In an exemplary embodiment, the diameter of the Si nanowire may be in the range of about 2-30 nm. The nanowire used may have an aspect ratio of length to diameter in a range of about 500-1500. The nanocrystals may comprise colloidal metal, such as gold, or quantum dots.

The nanocrystals may comprise semiconducting or super paramagnetic metal oxides such as iron oxides. Some variations include multiple sensors per component that detect the same biomarker, diverse concentration strengths of the same biomarker, and combinations of multiple biomarkers in an array or assay panel.

The conducting polymers, nanowires and nanocrystals used in FET-based sensors for use in a health and wellness analytical toilet described herein may be exploited for their optical, magnetic and electrical properties to detect various analytes. Their optical, magnetic and electrical properties may be tuned based on their size, how they are made, composition and how they are functionalized. A variety of transduction methods may be used to convert a binding event of a biomarker to a component in a sensor to a detectable and monitorable digital signal. The digital signal may comprise conductivity, resistance, voltage, conductance, fluorescence, spectroscopic, pH, magnetic changes or a combination thereof. In an exemplary embodiment, conductance or voltage or both the conductance and voltage in a FET-based sensor may be monitored when sensing for a biomarker. The conductance or voltage or both the conductance and voltage may be monitored with respect to time when a biomarker interacts with the sensor.

In some embodiments, conducting polymers, nanowires and nanocrystals used in FET-based sensors for use in a health and wellness analytical toilet described herein may be functionalized with one or more monoclonal antibody receptors. The receptors may be covalently attached. Antibody receptors may be used to detect one or more viruses. Such viruses may include DNA, RNA or reverse transcribing viruses. An individual sensor may comprise only one type of antibody to target and detect a specific virus, such as influenza A, adenovirus, covid-19 or ebola. In other embodiments, a sensor may comprise two or more antibodies to target and detect two or more different types of viruses.

In other embodiments, conducting polymers, nanowires and nanocrystals used in FET-based sensors for use in a health and wellness analytical toilet described herein may be functionalized with one or more monoclonal antibodies to detect pathogens that cause diseases such as cancer. Cancerous tumor cells release antigens that can be detected. These antigens may be proteins, peptides or polysaccharides. In an exemplary embodiment, a FET-based sensor in an analytical toilet may comprise one or more antibodies to detect antigens released by cancerous cells. Antigens are biomarkers released by cancerous cells may also be referred to as tumor markers. Such biomarkers may include CA 15-3 from breast cancer cells. Prostate specific antigen (PSA) found in prostate cancer cells. CA-125 antigen biomarker commonly found in ovarian cancer cells. Carcinoembryonic antigen (CEA) found in colorectal cancer cells.

Other biomarkers that may be detected by a FET-based sensor in an analytical toilet described herein include leucine-rich α-2-glycoprotein (LRG1), isoform-1 of multimerin-1 (MMRN1), 5100 calcium-binding protein A8 (S100A8), serpin B3 (SERPINB3) and differentiation-44 antigen (CD44) for cervical cancer. Biomarkers bladder-tumor-associated antigen, nuclear matrix protein 22 (NMP22), Calreticulin, clusterin, cystatin B, proepithelin, UHRF1, bladder tumor antigen (BTA), human complement factor H related protein (hCFHrp), nuclear matrix protein 22 (NMP22), angiopoeitin (ANG), apolipoprotein E (APOE), interleukin-2 (IL-2), interleukin-6 (IL-6), interleukin-8 (IL-8), interleukin-10 (IL-10), interleukin-12 (IL-12), interleukin-18 (IL-18), interleukin-1ra (IL-1ra), TNF-α, MMP-9, MMP-10, plasminogen activator inhibitor 1 (PAI-1), Semenogelin-2, Vascular endothelial growth factor (VEGF), Coronin-1A, DJ-1, PARK7, Gamma Synuclein, Apo-A1, UP1, soluble Fas, ORM1, HtrA1, hyaluronidase, CP1, CCL18, BLCA-4 and α-1B-glycoprotein for bladder cancer. Collagen α-1(III) peptide, collagen α-1(I) peptide, TMPRSS2-ERG and PCA3 biomarkers for prostate cancer. Cathepsin D, NMP22, creatinine, microalbumin, sodium (Na) and potassium (K) biomarkers for renal cancer. Eosinophil-derived Neurotoxin C-terminal Osteopontin fragments and Bcl-2 biomarkers for ovarian cancer. Matrix metallopeptidase-9 (MMP-9), HER-2 and ADAM12 biomarkers for breast cancer. Cystatin SN biomarker for colorectal cancer. IL-6, MMP9 biomarkers for multiple myeloma. It should be noted that some biomarkers are indicative of more than one type of cancer. It also should be noted that this is not an exhaustive list.

Some biomarkers may be indicative of injury or trauma. For example, a FET-based sensor in an analytical toilet described herein may be used to detect at least one biomarker released as a result of a kidney injury. These include urinary neutrophil gelatinase-associated lipocalin (NGAL), cystatin C (CyC), clusterin (CLU), hepatocyte growth factor (HGF), π-glutathione-S-transferase (π-GST), α-GST, kidney injury molecule-1 (KIM-1), osteopontin (OPN), renal papillary antigen (RPA-1), albumin, β2-microglobulin, trefoil factor-3 or urea.

A FET-based sensor in an analytical toilet described herein may be used to detect at least one biomarker released as a result of cardiovascular disease. This includes N-terminal pro-BNP (NT-proBNP), C-type natriuretic peptide (CNP), mRNA in urine supernatant (US-mRNA), adrenodoxin (ADX), eosinophil cationic protein (ECP), fetuin B (FETUB), growth differentiation factor 15 (GDF15), guanine deaminase (GUAD) or neurogenic notch homolog protein 1 (NOTCH1).

A FET-based sensor in an analytical toilet described herein may be used to detect at least one biomarker released as a result of a brain disease. This includes azelaic acid, N-methylnicotinamide, α-hydroxybutyrate, choline, formate, and N-methylnicotinamide, oxaloacetate or acetone biomarkers for bipolar disorder. Taurine, glutamate, N-acetyl glycoprotein, 3-(3-hydroxyphenyl)-3-hydroxypropanoic acid, five-carbon sugars, ribose, fructose, 1,2,3-butanetriol and propylene glycol biomarkers for autism. Glucosamine, glutamic acid, vanilmandelic acid, creatinine, α-ketoglutaric acid (α-KG), citrate, valine and glycine for schizophrenia. Serum albumin, apolipoprotein A-I, heparan sulfate proteoglycans (HSPGs), malonate, N-methylnicotinamide, m-hydroxyphenylacetate, hippuric acid, quinolinic acid or tyrosine biomarkers for depression.

A FET-based sensor in an analytical toilet described herein may also be used to detect at least one biomarker released as a result of various diseases such as fibrinogen for chronic obstructive pulmonary disease (COPD) or galactomannan for invasive aspergillosis.

A FET-based sensor in an analytical toilet described herein may also be used to detect nitrites for the presence of bacterial cystitis. Bacterial cystitis is commonly referred to as urinary tract infection (UTI). A FET-based sensor in an analytical toilet described herein may also be used to detect ketones such as acetoacetate (AcAc), Acetate (Acetone) or Beta-hydroxybutyrate (BHB) for the presence of diabetic ketoacidosis (DKA).

A component in a FET-based sensor in an analytical toilet described herein may be functionalized with peptide nucleic acid (PNA). PNA can be used as a gene sensor. A PNA is a non-charged variant of DNA and has high selectivity toward complementary DNA sequences. A PNA sensor is very sensitive with almost no electrochemical response toward DNA with one base mismatch. A PNA-based sensor may be used for detection of the DNA sequence responsible for sickle cell anemia.

A FET-based sensor in an analytical toilet described herein may be able to detect one or more viruses. The detectable viruses may be from the coronavirus class including alphacoronovirus, betacoronovirus, gammacoronavirus or deltacoronavirus. More specifically, these viruses may include SARS-CoV-2 (also known as COVID-19) or SARS-CoV. A component in a FET-based sensor may be functionalized with angiotensin converting enzyme 2 (ACE2) antibody as a receptor. The ACE2 receptor interacts with the spike protein on the surface of the SARS-COV-2 virus.

In an exemplary embodiment, sensors used in a health and wellness analytical toilet described herein are capable of detecting non-biomarker molecules. Such molecules may comprise prescription drugs, recreational drugs or illicit drugs. These may include amphetamines, nicotine, cannabinoids, opioids, cocaine, heroin, ethanol, methanol, pharmaceuticals or other various stimulants or depressants.

In an exemplary embodiment, sensors used in a health and wellness analytical toilet described herein are capable of multiplexed detection. Multiplexed detection is necessary for simultaneous detection of multiple biomarkers such as proteins. This is critical for reliable detection of complex diseases such as cancer. In some embodiments, FETS comprising both n-type and p-type Si nanowires with different receptors within the same sensor may be required for reliable cancer and other disease detection.

In some instances, the high ionic strength environment in a health and wellness analytical toilet from excreta may adversely affect the accuracy and precision of the FET-based biomarker sensor. In some embodiments, a biomolecule permeable layer may be located over the sensor. The biomarker permeable layer may be substantially impermeable to ions such that only biomarkers are able to pass through the layer and approach the sensor. The layer may increase the effective Debye screening length in the region immediately adjacent to the sensor surface. This may allow detection of biomolecules in high ionic strength solutions in real-time. In some embodiments, the layer may only be permeable to a target analyte. In some embodiments, the layer may be only permeable to a class of analytes. The layer may be comprised of a membrane. The layer may be porous. The layer may be comprised of a polymer. The polymer may be comprised of polyethylene glycol.

In some embodiments, BioFET-based sensors in a health and wellness analytical toilet may be combined with other methods of biomarker detection. Additional biomarkers may be measured via a miniaturized mass spectrometer. Alternatively, additional biomarkers may be measured using gas chromatography integrated into the toilet body or positioned adjacent to the toilet. Additional biomarkers may also be measured using fluorescence spectrometry. A fluorescent tag may be covalently or ionically attached to a target molecule. These tags may be a protein, antibody, peptide or amino acid. These tagged molecules may then be used to detect a specific target such as an antigen. In some instances, two or more detection methods, such as those described herein, may be used to detect the same biomarker.

In various exemplary embodiments, microfluidic systems may be used to isolate and transport a sample, add and mix reagents if appropriate, and test the sample for one or more biomarkers on a small scale (i.e., sub-millimeter scale) in a health and wellness analytical toilet described herein. The microfluidic system may comprise an open microfluidic system, continuous-flow microfluidic system, droplet-based microfluidic system, digital microfluidic system, nanofluidic system, paper-based microfluidic system or combinations thereof.

A microfluidic-based biomarker detection system may be located on a microfluidic chip (MFC). In a preferred embodiment, the MFC includes a test chamber with a lab-on-chip ("LoC") (also known as "test-on-chip"). The LoC may be designed to perform one or more laboratory tests. In various exemplary embodiments, one or more microfluidic chips (MFCs) may be removed or added to the toilet system as desired or needed at any given time, such as for different biomarker tests. In an exemplary embodiment, a DNA microfluidic chip may be used as a component in a biomarker sensor in a health and wellness analytical toilet. The DNA chip may comprise a DNA microarray, such as the GenChip DNAarray (Affymetrix, Santa Clara, CA, USA). The DNA microarray comprises one or more pieces of DNA (probes) for biomarker detection. The MFC may comprise one or more affixed proteins in an array-like fashion. In an exemplary embodiment, the proteins are monoclonal antibodies for detection of antigens.

Following use of the sensor, the toilet may prepare the sensor for future analysis by removing from the test area waste products and other things that might contaminate the next analysis. This could include flushing the sensor, adding a buffer or stabilizing solution, or adding a gas to remove all liquid from the sensor. There are various options to clean, sanitize, and/or prepare the various components of the involved between uses of the toilet. In one preferred embodiment, hot water is run through the fluidic circuit. In another preferred embodiment, oxygenated water is run through the fluidic circuit. In yet another preferred embodiment, a gas is run through the fluidic circuit to remove any liquid from being in contact with the sensor. Alternatively, cleaning and/or preservation agents are run through the fluid circuit. In still another embodiment, if an analyte receptor, such as an antibody receptor, is used in one or more sensors, the sensors are washed with a solution comprising one or more molecules at a predetermined concentration that can interact with and bind with the receptors in a known and predictive manner. This may be necessary when water or other solvent alone may not be sufficient to displace bound analytes, such as biomarkers, in order to clean the sensor. This cleaning method can act as an indicator to show that the sensors are washed and cleared of analytes before the next subject utilizes the toilet. The analytes may be further cleared from the sensor components using a cleaning or preservation agent dispensed from the toilet.

Additionally, temperature can be critical to the preparation, testing, or post processing of the sensor, the fluidic circuit, or the sample. As such, temperature controls may be included to accommodate those need. The controls could be built into the toilet, built into a fluidic circuit, or a result of adding a reagent to the sample. In one preferred embodiment, a resistive wire acts as a heat source to warm the sample and/or the sensor.

In various exemplary embodiments, the analytical toilet includes additional health and wellness sensors that may be located in a variety of location. In some embodiments, the seat may contain health and wellness sensors to measure pulse, blood pressure, blood oxygenation, electrocardiography, body temperature, body weight, excreta content, excreta weight, excreta volume, excreta temperature, excreta density, excreta flow rate, and other health and wellness indicators. In a preferred embodiment, the seat is attached to the toilet via a powered quick disconnect system that allows the seat to be interchangeable. This facilitates installing custom seats to include user-specific tests based on known health conditions. It also facilitates installing upgraded seats as sensor technology improves.

In various exemplary embodiments, the lid may contain health and wellness sensors that interact with the user's back or that analyze gases in the bowl after the lid is closed.

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. A method for obtaining health and wellness information about an individual, comprising:
   providing an analytical toilet comprising:
      a bowl adapted to receive excreta from the individual; and
      a sensor for measuring at least one characteristic of the individual or the excreta;
   a controller receiving data from the sensor and using the data to determine what additional information is needed to evaluate that data;
   the controller sending a prompt to the individual via a device to solicit the additional information from the individual;
   the processor receiving the information from the device; and
   processing the data from the sensor and from the device to determine the health and wellness information.

2. The method of claim 1, wherein the sensor measures one or more of pulse, blood pressure, blood oxygenation, and electrocardiography.

3. The method of claim 1, wherein the sensor detects one or more of body temperature and body weight.

4. The method of claim 1, wherein the sensor detects one or more of excreta content, excreta weight, excreta volume, excreta temperature, excreta density, and excreta flow rate.

5. The method of claim 1, wherein the controller obtains a list of potential health and wellness conditions associated with the individual, analyzes sensor data to add or remove conditions on the list, prompts the individual to provide more information, and uses the information to further add or remove conditions to or from the list.

6. The method of claim 5, wherein the list of possible health or wellness conditions comprises the user having taken in or failed to take in a medicament and the additional information requested is useful in determining if or when the medicament was taken.

7. The method of claim 5, wherein the additional information requested is related to the user's recent food and drink intake.

8. The method of claim 5, wherein the additional information requested is related to the user's recent physical activity.

9. The method of claim 5, wherein the additional information requested is related to whether the user is experiencing symptoms associated with a possible health or wellness condition on the list.

10. The method of claim 1, wherein the controller creates a list of potential conditions correlated to the sensor data.

11. The method of claim 10, wherein the controller sends prompts to the individual based on the list.

12. The method of claim 11, wherein the controller removes conditions from the list or adds conditions to the list based on responses to the prompts.

13. The method of claim 1, wherein the sensor is selected from the group consisting of imaging cameras, spectrometers, volume measurement devices, weight sensors, temperature gauges, chromatographs, and gas analyzers.

14. The method of claim 1, wherein the prompt comprises at least one question or instruction presented to the user audibly.

15. The method of claim 1, wherein the request for additional information is a result of data from the sensor that deviates from a well-established trend for that user.

16. The method of claim 1, wherein the request for additional information is a result of data from the sensor that deviates from a well-established trend for a population of people.

17. A system for obtaining health and wellness information about an individual, comprising:
   an analytical toilet comprising:
      a bowl adapted to receive excreta from the individual; and
      a sensor for measuring at least one characteristic of the individual or the excreta;
   a controller that receives data from the sensor and using the data to determine what additional information is needed to evaluate the data;
   a prompt to the individual to solicit the additional information; and
   the controller receives responses from the individual and uses the responses to further analyze the sensor data.

18. The system of claim 17, wherein the controller creates a list of potential conditions correlated to the sensor data.

19. The system of claim 18, wherein the controller sends prompts to the individual based on the list.

20. The system of claim 19, wherein the controller removes conditions from the list or adds conditions to the list based on responses to the prompts.

* * * * *